(12) United States Patent
Itoh et al.

(10) Patent No.: US 7,399,877 B2
(45) Date of Patent: Jul. 15, 2008

(54) PHOSPHOLIPID DERIVATIVE

(75) Inventors: Chika Itoh, Kanagawa (JP); Syunsuke Ohhashi, Kanagawa (JP); Kazuhiro Kubo, Kanagawa (JP); Tohru Yasukohchi, Kanagawa (JP); Hiroshi Kikuchi, Tokyo (JP); Norio Suzuki, Chiba (JP); Miho Takahashi, Shizuoka (JP); Hitoshi Yamauchi, Tokyo (JP)

(73) Assignees: NOF Corporation, Tokyo (JP); Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/549,630

(22) PCT Filed: Mar. 19, 2004

(86) PCT No.: PCT/JP2004/003789

§ 371 (c)(1),
(2), (4) Date: Aug. 17, 2006

(87) PCT Pub. No.: WO2004/083219

PCT Pub. Date: Sep. 30, 2004

(65) Prior Publication Data

US 2007/0031481 A1    Feb. 8, 2007

(30) Foreign Application Priority Data

Mar. 20, 2003 (JP) ............................... 2003-077242

(51) Int. Cl.
C07F 9/02 (2006.01)
(52) U.S. Cl. ..................................................... 558/174
(58) Field of Classification Search .................. 558/174
See application file for complete search history.

(56) References Cited

U.S. PATENT DOCUMENTS

| | | | |
|---|---|---|---|
| 5,142,036 A | 8/1992 | Akimoto et al. | |
| 5,173,219 A | 12/1992 | Kim | |
| 5,395,619 A | 3/1995 | Zalipsky et al. | |
| 5,540,935 A | 7/1996 | Miyazaki et al. | |
| 5,631,018 A | 5/1997 | Zalipsky et al. | |
| 6,344,576 B1 | 2/2002 | Eibl | |
| 6,436,905 B1 | 8/2002 | Tonge et al. | |
| 2002/0147136 A1* | 10/2002 | Von Wronski et al. | 514/8 |
| 2003/0144247 A1 | 7/2003 | Kuwano et al. | |
| 2005/0220856 A1 | 10/2005 | Itoh et al. | |
| 2006/0110436 A1 | 5/2006 | Ohhashi et al. | |
| 2006/0210618 A1 | 9/2006 | Kubo et al. | |

FOREIGN PATENT DOCUMENTS

| | | |
|---|---|---|
| EP | 0373621 | 6/1990 |
| EP | 0657463 | 6/1995 |
| EP | 1279406 | 1/2003 |
| JP | 63-221837 | 9/1988 |
| JP | 2-163108 | 6/1990 |
| JP | 6-228012 | 8/1994 |
| JP | 7-242680 | 9/1995 |
| JP | 7-268038 | 10/1995 |
| JP | 9-255740 | 9/1997 |
| JP | 2002-522442 | 7/2002 |
| WO | 99/09955 | 3/1999 |
| WO | 00/08031 | 2/2000 |
| WO | 00/33817 | 6/2000 |
| WO | 01/05375 | 1/2001 |
| WO | 01/74400 | 10/2001 |
| WO | 03/082882 | 10/2003 |
| WO | 2004/029104 | 4/2004 |
| WO | 2004/060899 | 7/2004 |

OTHER PUBLICATIONS

English language abstract of JP 63-221837, published Sep. 14, 1988.
English language abstract of JP 2-163108, published Jun. 22, 1990.

(Continued)

*Primary Examiner*—Yvonne Eyler
*Assistant Examiner*—Jennifer Y Cho
(74) *Attorney, Agent, or Firm*—Greenblum & Bernstein, P.L.C.

(57) ABSTRACT

A phospholipid derivative represented by the following formula (I) wherein $R^1CO$ and $R^2CO$ independently represent an acyl group; $R^3$ represents hydrogen atom, or a hydrocarbon group; symbol "a" represents an integer of 0 to 4; symbol "b" represents 0 or 1, provided that when a is 0, b is 0; X represents hydrogen atom, an alkali metal atom, an ammonium, or an organic ammonium; $A^1O$ and $A^3O$ represent an oxyalkylene group containing oxyethylene group, wherein the ratio of the oxyethylene group to the oxyalkylene group in $A^1O$ and $A^3O$ is 0.5 or larger in terms of a weight ratio; $A^2O$ represents an oxyalkylene group; symbols "m" and "q" represent an average molar number of added oxyalkylene groups; and symbol "n" represent an average molar number of added oxyalkylene groups; provided that m, n and q satisfy the following conditions: $5 \leq m \leq 600$, $1 \leq n \leq 45$, $0 \leq q \leq 200$, $10 \leq m+n+q \leq 600$, $0.04 \leq n/(m+n+q)$, and $q/(m+n+q) \leq 0.8$, which can thicken the water shell of liposome surface by suppressing the spreading of the polyalkylene oxide structure on the surface and thus increase stability of the liposome

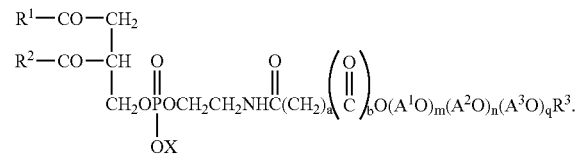

20 Claims, No Drawings

OTHER PUBLICATIONS

English language abstract of JP 6-228012, published Aug. 16, 1994.
English language abstract of JP 7-242680, published Sep. 19, 1995.
English language abstract of JP 7-268038, published Oct. 17, 1995.
English language abstract of JP 9-255740, published Sep. 30, 1997.
English language abstract of JP 2002-522442, published Jul. 23, 2002.
Harish M. Patel et al., "Inhibitory Effect on Cholesterol on the Uptake of Liposomes by Liver and Spleen", Biochimica et Biophysica Acta, vol. 761, pp. 142-151 (1983).
Carsten F. Gotfredsen et al., "Disposition of Intact Liposomes of Different Compositions and of Liposomal Degradation Products", Biochemical Pharmacology, vol. 32, No. 22, pp. 3381-3387 (1983).
Pharmaceutical Society of Japan, 106th Annula Meeting, Summaries of Symposia, pp. 336 (1986).
T.M. Allen et al., "Large Unilamellar Liposomes with Low Uptake into the Reticuloendothelial System", FEBS Letter, vol. 223, No. 1, pp. 42-46 (1987).
Alexander L. Klibanov et al., "Amphipathic Polyethyleneglycois Effectively Prolong the Circulation Time of Liposomes", FEBS Letter, vol. 268, No. 1, pp. 235-237 (1990).
Shingo Niimi et al., "Effects of Glucocorticoids on Deoxyribonucleic Acid (DNA) Synthesis Stimulated by Growth Factors in Cultured Rat Skin Fibroblasts", Chem. Pharm. Bul., vol. 38, No. 6, pp. 1633-1638 (1990).
Yong Serk Park et al., "Some Negatively Charge Phospholipid Derivatives Prolong the Liposome Circulation in Vivo", Biochimica et Biophysica Acta, vol. 1108, pp. 257-260 (1992).
Database WPI, Section Ch, Week 199546, Derwent Publications Ltd., London, GB, AN 1995-355265, XP002354282; accompanied by family member JP 07-242680 A.
T. Yuda et al., Biological and Pharmaceutical Bulletin, vol. 19, No. 10, pp. 1347-1351, 1996.
R. Zeisig et al., Biochimica et Biophysica Acta, vol. 1285, No. 2, pp. 237-245, 1996.
T.M. Allen et al., Biochimica et Biophysica Acta, vol. 1061, No. 1, pp. 56-64, 1991.

* cited by examiner

PHOSPHOLIPID DERIVATIVE

TECHNICAL FIELD

The present invention relates to a phospholipid derivative containing a polyoxyalkylene group comprising two or more kinds of alkylene oxides, as well as a surfactant, solubilizer, dispersing agent for cosmetics and lipid membrane structure containing the phospholipid derivative.

BACKGROUND ART

Microparticle drug carriers including liposomal formulations as typical examples and polypeptides such as protein drug are known to have poor retention in blood and be easily captured by the reticuloendothelial system (hereinafter abbreviated as "RES") such as liver and spleen when they are intravenously administered. The presence of RES is a serious obstacle when a microparticle drug carrier is utilized as a targeting type preparation, which delivers a medicament to organs other than RES, and as a sustained-release preparation, which allows a medicament retained in blood for a long period of time to control the release of the medicament.

Researches have so far been conducted to impart a microcirculation property to the aforementioned preparations. Some proposals have been made, including, for example, a method of maintaining a high blood concentration by reducing a size of liposomes in view of relative easiness of a control of physicochemical properties of lipid bilayers of liposomes (Biochimica et Biophysica Acta, Vol. 761, p. 142, 1983), a method of utilizing lecithin having a high phase transfer temperature (Biochemical Pharmacology, Vol. 32, p. 3381, 1983), a method of utilizing sphingomyelin instead of lecithin (Biochemical Pharmacology, Vol. 32, p. 3381, 1983), a method of adding cholesterol as a membrane component of liposomes (Biochimica et Biophysica Acta, Vol. 761, p. 142, 1983) and the like. However, no work based on these methods has been known so far that successfully provides a microparticle drug carrier having favorable retention in blood and being hardly taken up by RES.

As another approach for solution, researches have been made for providing a microcirculation property and escapability from RES by modification of membrane surfaces of liposomes with a glycolipid, glycoprotein, amino acid-lipid, polyethylene glycol-lipid or the like. Substances for the modification so far reported include, for example, glycophorin (The Pharmaceutical Society of Japan, the 106th Annual Meeting, Summaries of Symposia, p. 336, 1986), ganglioside GM1 (FEBS Letters, Vol. 223, p. 42, 1987), phosphatidylinositol (FEBS Letters, Vol. 223, p. 42, 1987), glycophorin and ganglioside GM3 (Japanese Patent Unexamined Publication (Kokai) No. 63-221837), polyethylene glycol derivative (FEBS Letters, Vol. 268, p. 235, 1990), glucuronic acid derivative (Chemical & Pharmaceutical Bulletin, Vol. 38, p. 1633, 1990), glutamic acid derivative (Biochimica et Biophysica Acta, Vol. 1108, p. 257, 1992), polyglycerin phospholipid derivative (Japanese Patent Unexamined Publication No. 6-228012), and the like.

As for modification of liposome surfaces with a polyethylene glycol-lipid, for example, it has been reported that water shell and stability in blood thereof are correlated, and if the water shell is thickened, the stability in blood is increased (Pharm. Tech. Japan, Vol. 12, No. 7, p. 925, 1996). For the purpose of thickening the water shell, an increased amount of added polyethylene glycol-lipid and an increased molecular weight of polyethylene glycol chain are examined. It is considered that, if the amount to be added or the molecular weight is increased as mentioned above, the horizontal three-dimensional spreading of the structure of the polyethylene glycol chain on the surface of a liposome can be suppressed, i.e., changing from a pancake structure to a mushroom structure or further to a brush structure, thereby the structure spreads in the vertical direction to thicken the water shell (Langmuir, Vol. 11, p. 3975). However, it has been reported that if the added amount is increased to become excess, the packing of liposome lipid membrane will be weaker, and the stability of the liposome is degraded (Biophysical Journal, Vol. 74, p. 1371, 1998). Moreover, if the molecular weight of the polyethylene glycol chain is increased, the coagulation point and viscosity become high, and difficulties in handling at an ordinary temperature arise at practical use, for example, inevitable dissolution step of the product.

DISCLOSURE OF THE INVENTION

An object of the present invention is to provide a novel phospholipid derivative. More specifically, the object of the present invention is to provide a phospholipid derivative that can be used in an amount similar to the amount of ordinary polyethylene glycol-phospholipids, and can thicken the water shell of the surface of lipid membrane structure, in particular, liposome, by suppressing the spreading of the polyalkylene oxide structure on the surface, thereby increases stability of liposome. Another object of the present invention is to provide a phospholipid derivative that is highly stable and highly safe for living bodies, and has a low coagulation point and thus favorable handling property at ordinary temperature. A further object of the present invention is to provide a phospholipid derivative that can be suitably used in the fields of solubilization and dispersion of physiologically active substances and the like, drug delivery systems such as liposomes, and cosmetics.

The inventors of the present invention conducted various researches to achieve the aforementioned objects. As a result, they succeeded in providing novel phospholipid derivatives represented by the following formula (I) or (II).

The present invention thus provides a phospholipid derivative represented by the following formula (I):

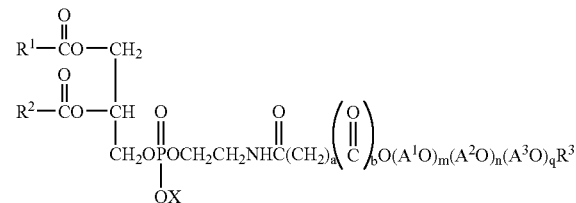

wherein $R^1CO$ and $R^2CO$ independently represent an acyl group having 8 to 22 carbon atoms; $R^3$ represents hydrogen atom, or a hydrocarbon group having 1 to 4 carbon atoms; symbol "a" represents an integer of 0 to 4; symbol "b" represents 0 or 1, provided that when a is 0, b is 0; X represents hydrogen atom, an alkali metal atom, an ammonium, or an organic ammonium; $A^1O$ and $A^3O$ independently represent an oxyalkylene group containing oxyethylene group and having 2 to 4 carbon atoms, wherein the ratio of the oxyethylene group to the oxyalkylene group having 2 to 4 carbon atoms in $A^1O$ and $A^3O$ is 0.5 or larger in terms of a weight ratio; $A^2O$ represents an oxyalkylene group having 3 or 4 carbon atoms; symbols "m" and "q" independently represent an average molar number of added oxyalkylene groups having 2 to 4 carbon atoms; and symbol "n" represent an average molar number of added oxyalkylene groups having 3 or 4 carbon atoms; provided that m, n, and q satisfy the following conditions: 5≦m≦600, 1≦n≦45, 0≦q≦200, 10≦m+n+q≦600, 0.04≦n/(m+n+q), and q/(m+n+q)≦0.8.

From the second aspect, the present invention provides a phospholipid derivative represented by the following formula (II):

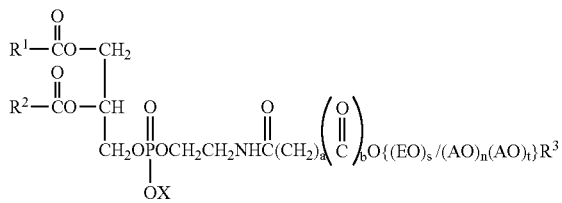

wherein R¹CO and R²CO independently represent an acyl group having 8 to 22 carbon atoms; R³ represents hydrogen atom, or a hydrocarbon group having 1 to 4 carbon atoms; symbol "a" represents an integer of 0 to 4; symbol "b" represents 0 or 1, provided that when a is 0, b is 0; X represents hydrogen atom, an alkali metal atom, an ammonium, or an organic ammonium; EO represents oxyethylene group; AO represents an oxyalkylene group having 3 or 4 carbon atoms; {(EO)s/(AO)t} represents a group consisting of randomly bonded oxyethylene groups and oxyalkylene groups having 3 or 4 carbon atoms, wherein the ratio of the oxyethylene groups to the oxyalkylene groups having 2 to 4 carbon atoms in {(EO)s/(AO)t} is 0.5 to 0.95 in terms of a weight ratio; symbol "s" represents an average molar number of added oxyethylene groups; and symbol "t" represent an average molar number of added oxyalkylene groups having 3 or 4 carbon atoms; provided that s and t satisfy the following conditions: 5≦s≦500, 0<t≦100, and 6≦(s+t)≦500.

From another aspect, the present invention provides a lipid membrane structure, preferably a liposome, containing the aforementioned phospholipid derivative represented by the aforementioned formula (I) or (II). The present invention also provides a pharmaceutical composition, which comprises the aforementioned lipid membrane structure that retains a medicament, and the aforementioned pharmaceutical composition, wherein the medicament is an antitumor agent. The present invention further provides a surfactant comprising the aforementioned phospholipid derivative represented by the aforementioned formula (I) or (II); a solubilizer comprising the aforementioned phospholipid derivative represented by the aforementioned formula (I) or (II); and a dispersing agent comprising the aforementioned phospholipid derivative represented by the aforementioned formula (I) or (II).

BEST MODE FOR CARRYING OUT THE INVENTION

In the aforementioned formulas (I) and (II), R¹CO and R²CO independently represent an acyl group having 8 to 22 carbon atoms, preferably 12 to 20 carbon atoms. An acyl group derived from a fatty acid can be preferably used as the aforementioned acyl group. Specific examples of R¹CO and R²CO include an acyl group derived from a saturated or unsaturated linear or branched fatty acid such as caprylic acid, capric acid, lauric acid, myristic acid, palmitic acid, palmitoleic acid, stearic acid, isostearic acid, oleic acid, linoleic acid, arachic acid, behenic acid, erucic acid, and lignoceric acid. R¹CO and R²CO may be the same or different.

R³ is hydrogen atom, or an alkyl group having 1 to 4 carbon atoms, preferably an alkyl group having 1 to 4 carbon atoms. As the alkyl group having 1 to 4 carbon atoms, an alkyl group having a linear or a branched chain, more specifically, methyl group, ethyl group, propyl group, or butyl group can be used, and methyl group is preferred. X represents hydrogen atom, an alkali metal atom, an ammonium, or an organic ammonium, preferably hydrogen atom, or an alkali metal atom. Specific examples include, for example, an alkali metal atom such as sodium and potassium, an organic ammonium such as triethylammonium, and the like. The symbol "b" represents an integer of 0 or 1. When b is 1, it is preferred that symbol "a" represents an integer of 1 to 4, more preferably 2 or 3. When b is 0, it is preferred that a is 0.

In the formula (I), A¹O and A³O each represent an oxyalkylene group containing oxyethylene group and having 2 to 4 carbon atoms.

Examples of the oxyalkylene group having 2 to 4 carbon atoms include, for example, oxyethylene group, oxypropylene group, oxytrimethylene group, oxybutylene group, oxytetramethylene group and the like.

A¹O and A³O are oxyalkylene groups containing oxyethylene group at a weight ratio of 0.5 or higher and having 2 to 4 carbon atoms. They may consist solely of oxyethylene groups, or copolymerized oxyethylene groups and oxyalkylene groups having 3 or 4 carbon atoms. When oxyalkylene groups having 3 or 4 carbon atoms are contained, the groups may be a block copolymer or random copolymer. One or more kinds of oxyalkylene groups having 3 or 4 carbon atoms may be used, and when two or more kinds of the groups are used, they may be polymerized as a block copolymer or random copolymer.

Examples of (A¹O)m and (A³O)q include, for example, a homopolymer of oxyethylene groups, a block polymer or random polymer of oxyethylene group and oxypropylene group, a block polymer or a random polymer of oxyethylene group and oxybutylene group, a block polymer or a random polymer, of oxyethylene group, oxypropylene group, and oxybutylene group, and the like.

The ratio of oxyethylene groups to oxyalkylene groups having 2 to 4 carbon atoms in (A¹O) m and (A³O) q, in terms of a weight ratio, may be 0.5 or more, preferably 0.6 or more, more preferably 1, which means they consist solely of oxyethylene groups. If the ratio of the oxyethylene groups is less than 0.5, the effect of retaining a water shell on the surface of lipid membrane structure to enhance the stability cannot be obtained. When they are block copolymers, the end of the polymer that participates in the bond with the phospholipid may preferably be oxyethylene group.

Depending on a combination, the phospholipid derivative may have an oxyalkylene group having 3 or 4 carbon atoms which directly bonds to the phospholipid, i.e., not by means of an oxyethylene group, at the end that participates in bonding to the phospholipid. When the above derivative is used for a pharmaceutical composition retaining a medicament, the retaining of the medicament may not be efficiently achieved. Therefore, the end for the bonding to the phospholipid may preferably be oxyethylene group.

The symbols m and q each represent an average molar number of the added oxyalkylene groups containing oxyethylene groups and having 2 to 4 carbon atoms, and m is 5 to 600, preferably 15 to 120. Symbol q is 0 to 200, preferably 0 to 120, more preferably 0 to 80. If m is smaller than 5, and the group is adjacent to the phospholipid bonding end, the retention of a medicament cannot be efficiently ahieved. If m is larger than 600, the effect derived from the polyoxyalkylene group consisting of $A^2O$, i.e., enhancement of the stability of the particles, may hardly be obtained. If q is larger than 200, the phospholipid derivative may not stably exist on particles when used in lipid membrane structures and the like, and the effect derived from the polyoxyalkylene group consisting of $A^2O$, i.e., enhancement of the stability of the particles, is also hardly obtainable.

In the formula (I), $A^2O$ represents an oxyalkylene group having 3 or 4 carbon atoms. Examples of the oxyalkylene group having 3 or 4 carbon atoms include, for example, oxypropylene group, oxytrimethylene group, oxybutylene group, and oxytetramethylene group, and oxypropylene group is preferred. One or more kinds of oxyalkylene groups having 3 or 4 carbon atoms may be used, and when two or more kinds of the oxyalkylene groups are copolymerized, they may be copolymerized as a block copolymer or a random copolymer. The symbol n represents an average molar number of the added oxyalkylene groups having 3 or 4 carbon atoms, and may be 1 to 45, preferably 2 to 30, more preferably 2 to 15. If n is less than 1, the effect of increasing the thickness of the water shell at the surface of lipid membrane structure particle may become low, and the increasing effects on the stability of the particles in an aqueous solution and on the retention of the particles in blood are hardly obtained. Further, the coagulation point becomes higher even at the same molecular weight, and the operability at an ordinary temperature becomes worse. If n is larger than 45, the phospholipid derivative may likely drop from the surfaces of lipid membrane structure particles, and the effect of retaining the water shell on the particle surfaces and enhancing effect on the stability are hardly obtained.

Moreover, m+n+q is 10 to 600, preferably 30 to 300.

If m+n+q is smaller than 10, the stabilizing effect may be low when the phospholipid derivative of the present invention is used as an additive for lipid membrane structures or a surfactant. Further, if m+n+q is larger than 600, the phospholipid derivative of the present invention cannot stably exist on the particles, and therefore more significant effect concerning stability of particles cannot be obtained compared with conventional substances. Furthermore, in the preparation, reactivity in the reaction of a polyalkylene oxide derivative and a phospholipid is lowered, and the viscosity of the polyalkylene oxide derivative of the aforementioned formula (2) will increase, which is not preferred because of reduced workability.

In order to further obtain efficiency of retention of a medicament within the aforementioned efficiently usable ranges of m, n, and q, the condition of $0.04 \leq n/(m+n+q)$ may be satisfied, and to enhance stability of the particles used, the condition of $q/(m+n+q) \leq 0.8$ may be satisfied.

In the formula (II), EO represents oxyethylene group, and AO represents an oxyalkylene group having 3 or 4 carbon atoms. Examples of the oxyalkylene group having 3 or 4 carbon atoms include, for example, oxypropylene group, oxytrimethylene group, oxybutylene group, and oxytetramethylene group, and oxypropylene group is preferred. $\{(EO)/s(AO)t\}$ is a group consisting of randomly bonded oxyethylene groups and oxyalkylene groups having 3 or 4 carbon atoms.

The symbol "s" represent an average molar number of the added oxyethylene groups, and the symbol "t" represents an average molar number of the added oxyalkylene groups having 3 or 4 carbon atoms. Symbol s may be 5 to 500, preferably 20 to 200. Symbol t is larger than 0 and 100 or less, preferably 1 to 100, more preferably 2 to 18. The sum of s and t is 6 to 500, preferably 20 to 200.

The ratio of oxyethylene groups to oxyalkylene groups having 2 to 4 carbon atoms in $\{(EO)/s(AO)t\}$ is 0.5 to 0.95, preferably 0.6 to 0.95, in terms of a weight ratio. If the ratio of the oxyethylene group is less than 0.5, the effect of retaining a water shell on the surface of lipid membrane structure to enhance stability cannot be obtained. Moreover, if the ratio is larger than 0.95, the effect of thickening the water shell on the membrane of the lipid membrane structure of the present invention cannot be obtained.

Although the methods for producing the compounds of the present invention represented by the formula (I) and (II) are not particularly limited, the compounds can be produced by reacting an activated ester derivative of a polyalkylene oxide compound or an activated carbonate derivative of a polyalkylene oxide derivative with a phospholipid compound. They can also be produced by reacting an activated ester derivative of a phospholipid compound with a polyalkylene oxide compound.

For example, the polyalkylene oxide derivative can be easily produced by reacting a polyalkylene oxide compound and dicarboxylic acid anhydride as described later. The polyalkylene oxide compound to be used can be produced by a known method. The phospholipid may be a natural phospholipid or synthetic phospholipid, and examples of the natural phospholipid include, for example, natural or synthetic phosphatidylethanolamine such as soybean phosphatidyldiethanolamine, hydrogenated soybean phosphatidyldiethanolamine, yolk phosphatidyldiethanolamine and hydrogenated yolk phosphatidyldiethanolamine, and the like. The phospholipid compound can also be produced by a known method.

The reaction of the polyalkylene oxide derivative and a phospholipid compound, or the reaction of the polyalkylene oxide compound and a phospholipid derivative can be performed in an organic solvent in the presence of a basic catalyst, and the reaction can be usually performed by using a dehydration condensation agent.

The type of the basic catalyst is not particularly limited, and examples include, for example, nitrogen-containing substances such as triethylamine, pyridine, dimethylaminopyridine, and ammonium acetate, organic salts such as sodium phosphate, sodium carbonate, sodium hydrogencarbonate, sodium borate, and sodium acetate, and the like. As the organic solvent, those having no reactive functional group such as hydroxyl group can be used without particular limitation. Examples include, for example, ethyl acetate, dichloromethane, chloroform, benzene, toluene, and the like.

The aforementioned activated ester derivative can be obtained by, for example, reacting a polyalkylene oxide compound or a phospholipid compound with an activator in the presence of a dehydration condensation agent. The type of the aforementioned activator is not particularly limited, and examples include, for example, N-hydroxysuccinimide, N,N'-disuccinimide carbonate, 1-hydroxybenzotriazole, N-hydroxy-5-norbornene-2,3-dicarboximide, N-hydroxyphthalimide, 4-hydroxyphenyldimethylsulfonium/methyl sulfate, isobutyl chloroformate, and the like. Among them, N-hydroxysuccinimide is preferred.

When a dehydration condensation agent is used, any dehydration condensation agent can be used without particular limitation so long as the agent can achieve dehydration condensation of a carboxyl derivative of polyalkylene oxide compound and amino group of phospholipid or hydroxyl group of N-hydroxysuccinimide or the like. Examples of the dehydration condensation agent include, for example, carbodiimide derivatives such as dicyclohexylcarbodiimide, and dicyclohexylcarbodiimide is especially preferred.

The compounds of the present invention represented by the aforementioned formula (I) or (II) can be used as phospholipids constituting a lipid membrane structure of liposome. By using the compounds of the present invention, circulating time in blood of liposome can be increased. This effect can be attained by adding a small amount of the compound of the present invention to a lipid membrane structure. Ordinary polyethylene glycol-phospholipids can enlarge the water shell by increasing the amount thereof added to a liposome. However, they have a problem in that, if the amount added is increased to become excess, the packing of liposome lipid membrane becomes weaker, thereby the stability of liposome becomes lowered. By using the phospholipid compound of the present invention as a constituent phospholipid of a lipid membrane structure, the hydrophobic chain at the end of the polyoxyethylene chain interrupts hydrogen bonds with water molecules, thereby two-dimensional spreading can be suppressed and the structure can three-dimensionally spread on the surface of a liposome, i.e., on a membrane of the lipid membrane structure. Accordingly, the thickness of the water shell on the surface of a liposome in an aqueous solution can be increased.

The amount of the compound of the present invention added to a lipid membrane structure may be an amount sufficient for effectively expressing efficacy of a medicament in vivo and is not particularly limited. The amount can be suitably selected depending on, for example, a type of medicament to be retained by the lipid membrane structure, a purpose of therapeutic or prophylactic treatment and the like, and a form of the lipid membrane structure. A type of a medicament retained by the lipid membrane structure provided by the present invention is not particularly limited. For example, compounds used as antitumor agents are preferred. Examples of such compounds include, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, paclitaxel, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercap top urine, fludarabine phosphate, actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mytomycin C, bleomycin sulfate, peplomycin sulfate, etoposide, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

Further, a gene or the like may be encapsulated in the lipid membrane structure of the present invention. The gene may be any of oligonucleotide, DNA, and RNA, and in particular, examples thereof include a gene for in vitro gene introduction such as transformation and a gene that act upon in vivo expression, for example, a gene for gene therapy, gene used in breeding of industrial animals such as laboratory animals and livestock, and the like. Examples of the gene for gene therapy include an antisense oligonucleotide, antisense DNA, antisense RNA, gene coding for a physiologically active substance such as enzymes and cytokines, and the like.

The aforementioned lipid membrane structure may further contain phospholipids and a sterol such as cholesterol, and cholestanol, another fatty acid having a saturated or unsaturated acyl group having 8 to 24 carbon atoms and an antioxidant such as α-tocopherol. Examples of the phospholipid include phosphatidylethanolamine, phosphatidylcholine, phosphatidylserine, phosphatidylinositol, phosphatidylglycerin, cardiolipin, sphingomyelin, ceramide phosphorylethanolamine, ceramide phosphorylglycerin, ceramide phosphorylglycerin phosphate, 1,2-dimyristoyl-1,2-deoxyphosphatidylcholine, plasmalogen, phosphatidic acid and the like, and they may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used.

The form of the lipid membrane structure of the present invention and the preparation method thereof are not particularly limited, and examples of the existence form thereof include, for example, a form of dried lipid mixture, form of dispersion in an aqueous solvent, dried or frozen form of the foregoing form and the like. The lipid membrane structure in the form of dried lipid mixture can be prepared by, for example, first dissolving lipid components to be used in an organic solvent such as chloroform, and drying up the solution under reduced pressure by using an evaporator or spray-drying the solution by using a spray dryer. Examples of the form of the lipid membrane structure dispersed in an aqueous solvent include unilamella liposomes, multilamella liposomes, O/W type emulsion, W/O/W type emulsion, spherical micelles, worm-like micelles, irregular layered structure and the like, and liposomes are preferred among them. A size of the lipid membrane structure in the dispersed state is not particularly limited. For example, the particle diameter of liposome or particle in emulsion is 50 nm to 5 μm, and the particle diameter of spherical micelle is 5 to 100 nm. When a worm-like micelle or irregular layered structure is formed, it can be considered that the thickness of one layer thereof is 5 to 10 nm, and such layers form a single layer.

The composition of the aqueous solvent (dispersion medium) is also not particularly limited, and the aqueous solvent may be, for example, a buffer such as phosphate buffer, citrate buffer, and phosphate-buffered physiological saline, physiological saline, a medium for cell culture or the like. The lipid membrane structure can be stably dispersed in these aqueous solvents. An aqueous solution of a sugar such as glucose, lactose, and sucrose, an aqueous solution of a polyhydric alcohol such as glycerin and propylene glycol and the like may be further added. In order to stably store the lipid membrane structure dispersed in such an aqueous solvent for a long period of time, it is desirable to minimize electrolytes in the aqueous solvent from a viewpoint of physical stability such as prevention of aggregation. Further, from a viewpoint of chemical stability of lipids, it is desirable to control a pH of the aqueous solvent to be in a range of from weakly acidic pH to around neutral pH (pH 3.0 to 8.0), and to remove dissolved oxygen by nitrogen bubbling. Further, when a lyophilized or spray-dried product is stored, for example, use of an aqueous sugar solution or aqueous polyhydric alcohol solution may enable effective storage at lyophilization and storage of an aqueous sugar solution. A concentration of these aqueous solvents is not particularly limited. When an aqueous sugar solution is used, for example, the concentration is preferably 2 to 20% (W/V), more preferably 5 to 10% (W/V), and when an aqueous polyhydric alcohol solution is used, the concentration is preferably 1 to 5% (W/V), more preferably 2 to 2.5% (W/V). In a buffer, a concentration of the buffering agent is preferably 5 to 50 mM, more preferably 10 to 20 mM. A concentration of the lipid membrane structure in an aqueous solvent is not particularly limited. A concentration of the total amount of lipids in the lipid membrane structure is preferably 0.1 to 500 mM, more preferably 1 to 100 mM.

The formulation of the lipid membrane structure dispersed in an aqueous solvent can be prepared by adding the aforementioned dried lipid mixture to an aqueous solvent and emulsifying the mixture by using an emulsifier such as a homogenizer, ultrasonic emulsifier, high pressure jet emulsifier or the like. Further, the aforementioned form can also be prepared by a method known as a method for preparing liposomes, for example, the reverse phase evaporation method, and the method for preparing dispersion is not particularly limited. When it is desired to control a size of the lipid membrane structure, extrusion can be performed under high pressure by using a membrane filter of even pore sizes or the like.

Examples of the method for drying the aforementioned lipid membrane structure dispersed in an aqueous solvent include ordinary lyophilization and spray drying. As the aqueous solvent used for these operations, an aqueous sugar solution, preferably aqueous sucrose solution or aqueous lactose solution, may be used as described above. When a lipid membrane structure dispersed in the aqueous solvent is first prepared and then successively dried, it becomes possible to store the lipid membrane structure for a long period of time. In addition, when an aqueous solution of a medicament is added to the dried lipid membrane structure, the lipid mixture is efficiently hydrated and thereby the medicament can be efficiently retained in the lipid membrane structure, which provides an advantageous effect. For example, a pharmaceutical composition can be prepared by adding a medicament to the lipid membrane structure, and thus the lipid membrane structure can be used as a pharmaceutical composition for therapeutic treatment and/or prevention of a disease. When the medicament is a gene, the composition can also be used as a gene delivery kit.

As for a formulation of the pharmaceutical composition, the formulation may be the lipid membrane structures retaining a medicament, as well as a mixture of a medicament and the lipid membrane structures. The term "retain" used herein means that a medicament exists inside the membranes of the lipid membrane structures, on the membrane surfaces, in the membranes, in the lipid layers, and/or on the lipid layer surfaces. An available formulation of the pharmaceutical composition and a method for preparation thereof are not particularly limited in the same manner as the lipid membrane structures. As for the available form, examples include a form of a dried mixture, a form of a dispersion in an aqueous solvent, and forms obtained by further drying or freezing said forms.

A dried mixture of lipids and a medicament can be produced by, for example, once dissolving lipid components and a medicament to be used in an organic solvent such as chloroform and then subjecting the resulting solution to solidification under reduced pressure by using an evaporator or spray drying by using a spray dryer. Examples of a form in which a mixture of lipid membrane structures and a medicament are dispersed in an aqueous solvent include, but not particularly limited thereto, multi-lamella liposomes, unilamella liposomes, O/W type emulsions, W/O/W type emulsions, spherical micelles, fibrous micelles, layered structures of irregular shapes and the like. A size of particles (particle diameter) as the mixture, a composition of the aqueous solvent and the like are not particularly limited. For example, liposomes may have a size of 10 nm to 2 μm, spherical micelles may have a size of 5 to 100 nm, and emulsions may have a particle diameter of 50 nm to 5 μm. A concentration of the mixture in the aqueous solvent is also not particularly limited. Several methods are known as methods for producing a mixture of lipid membrane structures and a medicament in the form of dispersion in an aqueous solvent. It is necessary to appropriately chose a suitable method depending on an available form of the mixture of lipid membrane structures and a medicament.

<Production Method 1>

Production Method 1 is a method of adding an aqueous solvent to the aforementioned dried mixture of lipids and a medicament and emulsifying the mixture by using an emulsifier such as homogenizer, ultrasonic emulsifier, high-pressure emulsifier, or the like. When it is desired to control the size (particle diameter), extrusion can be further performed under a high pressure by using a membrane filter having uniform pore sizes. In this method, in order to prepare a dried mixture of lipids and a medicament first, it is necessary to dissolve the medicament in an organic solvent, and the method has an advantage that it can make the best utilization of interactions between the medicament and lipid membrane structures. Even when the lipid membrane structures have a layered structure, a medicament can enter into the inside of the multiple layers, and thus use of this method generally provides a higher encapsulation efficiency of the medicament in the lipid membrane structures.

<Production Method 2>

Production Method 2 is a method of adding an aqueous solvent containing a medicament to dried lipid components obtained by dissolving the lipid components in an organic solvent and evaporating the organic solvent, and emulsifying the mixture. When it is desired to control the size (particle diameter), extrusion can be further performed under a high pressure by using a membrane filter having uniform pore sizes. This method can be used for a medicament that is hardly dissolved in an organic solvent, but can be dissolved in an aqueous solvent. When the lipid membrane structures are liposomes, they have an advantage that they can retain a medicament also in the part of internal aqueous phase.

<Production Method 3>

Production Method 3 is a method of further adding an aqueous solvent containing a medicament to lipid membrane structures such as liposomes, emulsions, micelles or layered structures already dispersed in an aqueous solvent. This method is limitedly applied to a water-soluble medicament. The addition of a medicament to already prepared lipid membrane structures is performed from the outside. Therefore, when the medicament is a polymer, the medicament cannot enter into the inside of the lipid membrane structures, and the medicament may be present in a form that it binds to the surfaces of lipid membrane structures. When liposomes are used as the lipid membrane structures, use of Production Method 3 may result in formation of a sandwich-like structure in which the medicament is sandwiched between liposome particles (generally called as a complex). An aqueous dispersion of lipid membrane structures alone is prepared beforehand in this production method. Therefore, decomposition of a medicament during the preparation need not be taken into consideration, and a control of the size (particle diameter) is also readily operated, which enables relatively easier preparation compared with Production Methods 1 and 2.

<Production Method 4>

Production Method 4 is a method of further adding an aqueous solvent containing a medicament to a dried product obtained by once producing lipid membrane structures dispersed in an aqueous solvent and then drying the same. In this method, a medicament is limited to a water-soluble medicament in the same manner as Production Method 3. A significant difference from Production Method 3 is a mode of presence of the lipid membrane structures and a medicament. That is, in Production Method 4, lipid membrane structures dispersed in an aqueous solvent are once produced and further dried to obtain a dried product, and at this stage, the lipid membrane structures are present in a state of a solid as fragments of lipid membranes. In order to allow the fragments of lipid membranes to be present in a solid state, it is preferable to use an aqueous solution of a sugar, preferably an aqueous solution of sucrose or aqueous solution of lactose, as the aqueous solvent as described above. In this method, when the aqueous solvent containing a medicament is added, hydration of the fragments of the lipid membranes present in a state of a solid quickly starts with the invasion of water, and thus the lipid membrane structures can be reconstructed. At this time, a structure of a form in which a medicament is retained in the inside of the lipid membrane structures can be produced.

In Production Method 3, when a medicament is a polymer, the medicament cannot enter into the inside of the lipid membrane structures, and is present in a mode that it binds to the surfaces of the lipid membrane structures. Production Method 4 significantly differs in this point. In Production Method 4, an aqueous dispersion of lipid membrane structures alone is prepared beforehand, and therefore, decomposition of the medicament during the emulsification need not be taken into consideration, and a control of the size (particle diameter) is also easy attainable. For this reason, said method enables relatively easier preparation compared with Production Methods 1 and 2. Besides the above mentioned advantages, this method also has advantages that storage stability for a pharmaceutical preparation is easily secure, because the method uses lyophilization or spray drying; when the dried preparation is rehydrated with an aqueous solution of a medicament, original size (particle diameter) can be reproduced; when a polymer medicament is used, the medicament can be easily retained in the inside of the lipid membrane structures and the like.

As other method for producing a mixture of lipid membrane structures and a medicament in a form of a dispersion in an aqueous solvent, a method well known as that for producing liposomes, e.g., the reverse phase evaporation method or the like, may be separately used. When it is desired to control the size (particle diameter), extrusion can be performed under a high pressure by using a membrane filter having uniform pore sizes. Further, examples of the method for further drying a dispersion, in which the aforementioned mixture of lipid membrane structures and a medicament is dispersed in an aqueous solvent, include lyophilization and spray drying. As the aqueous solvent in this process, it is preferable to use an aqueous solution of a sugar, preferably an aqueous solution of sucrose or an aqueous solution of lactose. Examples of the method for further freezing a dispersion, in which the aforementioned mixture of lipid membrane structures and a medicament is dispersed in an aqueous solvent, include ordinary freezing methods. As the aqueous solvent in this process, it is preferable to use an aqueous solution of sugar or aqueous solution of polyhydric alcohol in the same manner as the solution for the lipid membrane structures alone.

Lipids which can be added to the pharmaceutical composition may be suitably chosen depending on a type of a medicament to be used and the like. The lipids are used in an amount of, for example, 0.1 to 1000 parts by mass, preferably 0.5 to 200 parts by mass, based on 1 part by mass of a medicament when the medicament is not a gene. When the medicament is a gene, the amount is preferably 1 to 500 nmol, more preferably 10 to 200 nmol, with 1 μg of a medicament (gene).

The method for use of the pharmaceutical composition of the present invention which contains the lipid membrane structures may be suitably considered depending on a form thereof. The administration route for humans is not particularly limited, and either oral administration or parenteral administration may be used. Examples of dosage forms for oral administration include, for example, tablets, powders, granules, syrups, capsules, solutions for internal use and the like, and examples of dosage forms for parenteral administration include, for example, injections, drip infusion, eye drops, ointments, suppositories, suspensions, cataplasms, lotions, aerosols, plasters and the like. In the medicinal field, injections or drip infusion is preferred among them, and as the administration method, intravenous injection, subcutaneous injection and intradermal injection, as well as local injection to targeted cells or organs are preferred. Further, as for the cosmetic field, examples of forms of cosmetics include lotions, creams, toilet water, milky lotions, foams, foundations, lipsticks, packs, skin cleaning agents, shampoos, rinses, conditioners, hair tonics, hair liquids, hair creams and the like.

By using the compound of the present invention represented by the aforementioned formula (I) or (II) as a surfactant, a solubilized solution, emulsion, and dispersion can be obtained. When the surfactant of the present invention is used as an emulsifier, solubilizer, or dispersing agent, the emulsifier, solubilizer, or dispersing agent may solely contain the surfactant of the present invention, or may also contain other known components used for emulsification, solubilization, or dispersion. The form of the solubilized solution or dispersion is not limited, and examples include a solution in which a fat-soluble substance or the like is dissolved in a dispersion medium such as water and a buffer, or a dispersion in which a fat-soluble substance or the like is dispersed in a dispersion medium such as water and a buffer and the like.

Formulation of the emulsion and solubilized solution are not limited, and examples include a micelle solution formed with the surfactant of the present invention, i.e., a micelle solution in which micelles contain a fat-soluble substance in the inside thereof, an emulsion in which dispersed particles formed with the surfactant of the present invention and a fat-soluble substance or the like exist as colloidal particles or larger particles, and the like. Examples of the micelle solution include polymer micelle solutions in which dispersed particles have a diameter of 10 to 300 nm. The emulsion may be of O/W type, in which a fat-soluble substance is formulated in an oil phase, or W/O/W type, in which a liposoluble substance is formulated in an aqueous phase. The fat-soluble substance that can be solubilized or emulsified is not particularly limited, and examples thereof include a higher alcohol, ester oil, triglycerin, tocopherol, higher fatty acid, hardly water-soluble medicaments, and the like. The use as a dispersing agent in the field of cosmetics is also not particularly limited. For example, when a water-soluble substance such as ascorbic acid is retained in an internal aqueous phase of a lipid membrane structure, a fat-soluble substance such as tocopherol is retained in a lipid bilayer or the like, the objective substance can be more stably dispersed in an aqueous solution by using the compound of the present invention as a lipid membrane structure formulating agent. When the compound is used as a surfactant or a dispersing agent, the amount of the compound to be added is 0.1 to 20% by mass, preferably 0.5 to 7% by mass, more preferably 0.5 to 5% by mass, based on a total mass of an objective substance for solubilization, dispersion, emulsification or the like.

EXAMPLES

The present invention will be explained more specifically with reference to the following examples. However, the scope of the present invention is not limited to these examples Synthesis Example 1

Synthesis of monomethyl-polyoxypropylene/polyoxyethylene-succinyl (Molecular Weight: 2000)-distearoylphosphatidylethanolamine (1) Synthesis of monomethyl-polyoxypropylene/polyoxyethylene glycol Methanol (160 g, 5 mol) and a 28% solution of sodium methylate in methanol (118.2 g) were placed into a 5 L-volume autoclave. After the inside of the system was replaced with nitrogen gas, the temperature was increased to 85° C., and propylene oxide (71583.2 g, 27.3 mol) was continuously introduced with pressurization and stirring under the conditions of 100 to 120° C. and 0.6 MPa or lower. After completion of the addition of propylene oxide, the reaction was continued at 115±5° C. for 2 hours with stirring, then the reaction mixture was treated at 75 to 85° C. and 6 to 14 kPa for 1 hour with introducing nitrogen gas to evaporate unreacted propylene oxide, and cooled to 50° C., and 1636 g of the product was extracted. Then, the temperature of the inside of the 5 L-volume autoclave was raised to 100° C., and ethylene oxide (2040 g, 46.4 mol) was continuously introduced with pressurization into the remaining product under the conditions of 100 to 130° C. and 0.6 MPa or lower with stirring. After completion of the addition of ethylene oxide, the reaction was continued with stirring at 120±5° C. for 1 hour. Then, after the reaction mixture was treated at 75 to 85° C. and 6 to 14 kPa for 1 hour with introducing nitrogen gas to evaporate unreacted ethylene oxide. Then, the reaction mixture was adjusted to pH 7 with addition of 85% phosphoric acid and subjected to a dehydration treatment at 80 to 110° C. and 6 to 14 kPa for 1 hour, and the generated neutralization salt was removed by filtration to obtain 1400 g of monomethyl-polyoxypropylene/polyoxyethylene glycol with a molecular weight of 2077. The molecular weight after the alkylene oxide addition reaction was calculated by measuring the hydroxyl value of the neutralized sample.

(2) Synthesis of monomethyl-polyoxypropylene/polyoxyethylene (Molecular Weight: 2000)-succinimidylsuccinate The monomethyl-polyoxypropylene/polyoxyethylene glycol (50 g, 0.025 mol) obtained above was added with sodium acetate (0.2 g, 2.4 mmol). The mixture was made uniform by warming at 100° C., then added with succinic anhydride (2.75 g, 0.027 mol), and reacted at 110° C. for 8 hours. The reaction mixture was cooled, and then added with isopropyl alcohol (200 mL) to obtain crystals of monomethyl-polyoxypropylene/polyoxyethylene-succinate. The crystals were added with toluene (150 mL), and dissolved by warming at 40° C. Then, the solution was added with N-hydroxysuccinimide (3.45 g, 0.03 mol) and dicyclohexylcarbodiimide (6.18 g, 0.03 mol), and reacted at 40° C. for 2 hours. After the reaction was completed, the reaction mixture was filtered to obtain 45 g of crude activated monomethyloxypropylene/polyoxyethylene-succinimidylsuccinate represented by the following formula (5).

(3) Synthesis of monomethyl-polyoxypropylene/polyoxyethylene (Molecular Weight: 2000)-succinyldistearoylphosphatidylethanolamine Distearoylphosphatidylethanolamine (14.96 g, 0.02 mol) was added with toluene (75 mL), and warmed to 60° C. to obtain a phospholipid solution in toluene. Separately, disodium hydrogenphosphate (7.2 g, 0.05 mol) was added with distilled water (7.5 mL) and 30% aqueous sodium hydroxide (0.75 mL) and dissolved by warming to obtain a phosphate buffer. This phosphate buffer was added to the phospholipid solution in toluene, and stirred at 60° C. to obtain a buffered phospholipid mixture. This buffered phospholipid mixture was added with crude activated monomethyloxy-propylene/polyoxyethylene-succinimidylsuccinate of the formula (2) (22.15 g, 0.01 mol), and reacted at 60° C. for 5 hours. After the reaction was completed, the reaction mixture was neutralized to pH 7 with 0.5 N aqueous sodium hydroxide. Then, the reaction mixture was added with sodium sulfate (150 g) and stirred for 1 hour to perform dehydration.

After the dehydration step, the insoluble solids were removed by filtration, and the filtrate was added with 400 mL of hexane, and stirred for 1 hour to deposit crystals. These crystals were collected by filtration. The crude crystals obtained were dissolved in ethyl acetate (100 mL) by warming at 50° C., added with 0.5 g of Kyoward 700 and 0.5 g of Kyoward 1000 (Kyowa Chemical Industry) as adsorbents, and stirred for 30 minutes. Kyoward was removed by suction filtration, and the resulting filtrate was added with hexane (50 mL) to deposit crystals. These crystals were collected by filtration. The crystals were added with acetone (300 mL) and dissolved by warming at 50° C., and the solution was filtered while it was hot to remove unreacted phospholipid as insoluble matter. Then, the filtrate was cooled to 15° C. or lower to deposit crystals. These crystals were collected by filtration. The crystals obtained were added with ethyl acetate (180 mL), and dissolved by warming at 60° C., and then the solution was cooled to 15° C. or lower to deposit crystals. These crystals were collected by filtration. When insoluble solids remained at the time of the dissolution by warming, the solids were removed by filtration, and the filtrate was used in the following step. In a similar manner, the crystals obtained were dissolved again in ethyl acetate (200 mL) by warming, and the crystals deposited by addition of hexane (100 mL) were collected by filtration to obtain 50 g of crystals with a final purity of 98%. The yield was 90.8% based on the activated polyoxyethylene. The product was analyzed by thin layer chromatography (TLC) utilizing a silica gel plate. A mixed solvent of chloroform and methanol at a weight ratio of 85:15 was used as a developing solvent, and substances contained were identified and quantified by coloration with iodine vapor on the basis of comparison with standard substances of known amounts.

Synthesis Example 2

Synthesis of monomethyl-polyoxypropylene/polyoxyethylene glutaryl (Molecular Weight: 2000)-distearoylphosphatidylethanolamine (1) Synthesis of monomethyl-polyoxypropylene/polyoxyethylene (Molecular Weight: 2000)-succinimidylglutarate The monomethyl-polyoxypropylene/polyoxyethylene glycol (50 g, 0.025 mol) obtained above was added with sodium acetate (0.2 g, 2.4 mmol), and the mixture was made uniform by warming at 100° C. Then, the mixture was added with glutaric anhydride (3.08 g, 0.027 mol), and reacted at 110° C. for 8 hours. The reaction mixture was cooled, and then added with isopropyl alcohol (200 mL) to obtain crystals of monomethyl-polyoxypropylene/polyoxyethylene-glutarate. The crystals were added with toluene (150 mL), and dissolved by warming at 40° C. Then, the solution was added with N-hydroxysuccinimide (3.45 g, 0.03 mol) and dicyclohexylcarbodiimide (6.18 g, 0.03 mol), and reacted at 40° C. for 2 hours. After the reaction was completed, the reaction mixture was filtered to obtain 46 g of crude activated monomethyloxy-propylene/polyoxyethylene-succinimidylglutarate represented by the following formula (5).

(2) Synthesis of monomethyl-polyoxypropylene/polyoxyethylene (Molecular Weight: 2000)-glutaryldistearoylphosphatidylethanolamine The crude activated monomethyloxy-propylene/polyoxyethylene-succinimidylglutarate (22 g) was used to obtain 51 g of crystals of monomethyl-polyoxypropylene/polyoxyethylene (molecular weight: 2000)-glutaryldistearoylphosphatidylethanolamine in the same manner as in Synthesis-Example 1-(3).

Synthesis Example 3

Synthesis of monomethyl-polyoxypropylene/polyoxyethylene-carbamyl (Molecular Weight: 2000)-distearoylphosphatidylethanolamine The monomethyl-polyoxypropylene/polyoxyethylene glycol obtained in Synthesis Example 1-(1) (molecular weight: 2000, 50 g, 25 mmol) was used, and the material was added with sodium carbonate (53 g, 500 mmol) and toluene (200 mL), and warmed to 75° C. The reaction mixture was added with p-nitrophenyl chloroformate (12.6 g, 62.5 mmol), and reacted for 9 hours. The reaction mixture was cooled to 65° C., then added with distearoylphosphatidylethanolamine (28.1 g, 37.5 mmol), and reacted for 7.5 hours.

After the sodium carbonate was removed by filtration, the filtrate was added with hexane (500 mL) and cooled to 5° C., and the deposited crystals were collected by filtration. The crystals were added with acetone (200 mL), warmed to 50° C., and then filtered through a glass filter to remove the insoluble solids (step (B)). The filtrate was added with hexane (500 mL), and cooled to 5° C. The deposited crystals were collected by filtration, and then used in the step (C). In the step (C), the crystals were added with ethyl acetate (750 mL), dissolved at 65° C., stirred for 30 minutes, and then cooled to 5° C., and the deposited crystals were collected by filtration. The step (C) using ethyl acetate was similarly performed once more. The crystals were dissolved in ethyl acetate (750 mL), added with Kyoward 2000 (12 g) and Kyoward 700 (1 g, Kyowa Chemical Industry) as adsorbents, and stirred at 60° C. for 1 hour. After the adsorbents were removed by filtration, the filtrate was cooled to 5° C., and the deposited crystals were collected by filtration (step (D)). In a similar manner, the treatment of the step (D) using adsorbents was performed twice. The crystals were washed with hexane (300 mL), collected by filtration, and dried to obtain 38.2 g (yield: 54.6%) of the objective compound. As a result of TLC analysis performed in the same manner as in Synthesis Example 1, the purity was found to be 99.5%.

Synthesis Example 4

Synthesis of monomethyl-polyoxypropylene/polyoxyethylene (75/25) (Molecular Weight: 2000)-succinyldistearoylphosphatidylethanolamine (1) Synthesis of monomethyl-polyoxypropylene/polyoxyethylene (75/25) glycol Methanol (32 g, 1 mol) and a 28% solution of sodium methylate in methanol (SM-28, 21.4 g) were placed into a 5 L-volume autoclave. After the inside of the system was replaced with nitrogen gas, the temperature was increased to 85° C., and 435 g of propylene oxide and ethylene oxide uniformly mixed beforehand at a weight ratio of 75/25 was continuously introduced with stirring and pressurization under the conditions of 110 to 120° C. and 0.6 MPa or lower. After completion of the addition of propylene oxide and ethylene oxide (75/25), the reaction was continued at 115±5° C. for 1 hour with stirring. The reaction mixture was cooled to 50° C., and 200 g of the product was extracted. Then, the temperature in the 5 L-volume autoclave was raised to 100° C., and 1640 g of propylene oxide/ethylene oxide (75/25) were continuously introduced into the remaining product with pressurization and stirring under the conditions of 110 to 120° C. and 0.6 MPa or lower. After completion of the addition of ethylene oxide, the reaction was continued with stirring at 120±5° C. for 1 hour. Then, the reaction mixture was subjected to a treatment at 75 to 85° C. and 6 to 14 kPa for 1 hour with introducing nitrogen gas to evaporate unreacted propylene oxide/ethylene oxide (75/25). Then, the reaction mixture was adjusted to pH 7 with addition of 85% phosphoric acid, and subjected to a dehydration treatment at 80 to 110° C. and 6 to 14 kPa for 1 hour. The generated neutralization salt was removed by filtration to obtain 1600 g of monomethyl-polyoxypropylene/polyoxyethylene (75/25) glycol with a molecular weight of 2004.

(2) Synthesis of monomethyl-polyoxypropylene/polyoxyethylene (75/25) (Molecular Weight: 2000)-succinimidylsuccinate By using the monomethyl-polyoxypropylene/polyoxyethylene (75/25) glycol obtained above (50 g, 0.025 mol), 42 g of crude activated monomethyl-polyoxypropylene/polyoxyethylene-succinimidylsuccinate was obtained in the same manner as in Synthesis-Example 1-(2).

(3) Synthesis of monomethyl-polyoxypropylene/polyoxyethylene (75/25) (Molecular Weight: 2000)-succinyldistearoylphosphatidylethanolamine By using the crude activated monomethyl-polyoxypropylene/polyoxyethylene (75/25) (molecular weight: 2000)-succinimidylsuccinate of the aforementioned formula (2) (22.15 g, 0.01 mol), monomethyl-polyoxypropylene/polyoxyethylene (75/25) (molecular weight: 2000)-succinyldistearoylphosphatidylethanolamine was obtained with a purity of 95% and a yield of 90% in the same manner as in Synthesis Example 1-(3).

Synthesis Example 5

Synthesis of monomethyl-polyoxyethylene/polyoxypropylene/polyoxyethylene-succinyl (Molecular Weight: 2000)-distearoylphosphatidylethanolamine

(1) Synthesis of monomethyl-polyoxyethylene/polyoxypropylene/polyoxyethylene glycol (Molecular Weight: 2000)

Methanol (32 g, 1 mol) and a 28% solution of sodium methylate in methanol (21.4 g, SM-28) were placed into a 5 L-volume autoclave. After the inside of the system was replaced with nitrogen gas, the temperature was increased to 80° C., and ethylene oxide (931 g, 21.2 mol) was continuously introduced with pressurization and stirring under the conditions of 100 to 130° C. and 0.6 MPa or lower. After completion of the addition of ethylene oxide, the reaction was continued at 120±5° C. for 1 hour with stirring, and then the reaction mixture was treated at 75 to 85° C. and 6 to 14 kPa for 1 hour with introducing nitrogen gas to evaporate unreacted ethylene oxide. Subsequently, the temperature in the 5 L-volume autoclave was raised to 100° C., and propylene oxide (180 g, 3.1 mol) was continuously introduced into the remaining product with pressurization and stirring under the conditions of 110 to 120° C. and 0.6 MPa or lower. After completion of the addition of propylene oxide, the reaction with stirring was continued at 110 to 120° C. for 1 hour. Then, the reaction mixture was treated at 75 to 85° C. and 6 to 14 kPa for 1 hour with introducing nitrogen gas to evaporate unreacted propylene oxide. Subsequently, the temperature in the 5 L-volume autoclave was raised to 100° C., and ethylene oxide (931 g, 21.2 mol) was continuously introduced into the remaining product with pressurization and stirring under the conditions of 100 to 130° C. and 0.6 MPa or lower. After completion of the addition of ethylene oxide, the reaction with stirring was continued at 120±5° C. for 1 hour. The reaction mixture was adjusted to pH 7 with addition of 85% phosphoric acid, and subjected to a dehydration treatment at 80 to 110° C. and 6 to 14 kPa for 1 hour. The generated neutralization salt was removed by filtration to obtain 1670 g of monomethyl-polyoxyethylene/polyoxypropylene (3.2 mol)/polyoxyethylene glycol with a molecular weight of 2025.

(2) Synthesis of monomethyl-polyoxyethylene/polyoxypropylene/polyoxyethylene glycol (Molecular Weight: 2000)-succinimidylsuccinate By using the monomethyl-polyoxyethylene/polyoxypropylene/polyoxyethylene glycol obtained above (molecular weight: 2000, 50 g, 0.025 mol), 42 g of crude activated monomethyl-polyoxyethylene/polyoxypropylene/polyoxyethylene glycol (molecular weight: 2000)-succinimidylsuccinate was obtained in the same manner as in Synthesis Example 1-(2).

(3) Synthesis of monomethyl-polyoxyethylene/polyoxypropylene/polyoxyethylene glycol (Molecular Weight: 2000)-succinyldistearoylphosphatidylethanolamine By using the crude activated monomethyl-polyoxyethylene/polyoxypropylene/polyoxyethylene glycol (molecular weight: 2000)-succinimidylsuccinate of the aforementioned formula (2) (22.15 g, 0.01 mol), monomethyl-polyoxyethylene/polyoxypropylene/polyoxyethylene glycol (molecular weight: 2000)-succinyldistearoylphosphatidylethanolamine was obtained with a purity of 95% and a yield of 90% in the same manner as in Synthesis-Example 1-(3).

Synthesis Example 6

Synthesis of monomethyl-polyoxyethylene/polyoxypropylene/polyoxyethylene-carbamyl (Molecular Weight: 2000)-distearoylphosphatidylethanolamine The monomethyl-polyoxyethylene/polyoxypropylene/polyoxyethylene glycol obtained in Synthesis-Example 5-(1) (molecular weight: 2000, 50 g, 25 mmol) was used, and the material was added with sodium carbonate (53 g, 500 mmol) and toluene (200 mL), and warmed to 75° C. The reaction mixture was added with p-nitrophenyl chloroformate (12.6 g, 62.5 mmol), and reacted for 9 hours. The reaction mixture was cooled to 65° C., then added with distearoylphosphatidylethanolamine (28.1 g, 37.5 mmol), and reacted for 7.5 hours.

After the sodium carbonate was removed by filtration, the filtrate was added with hexane (500 mL) and cooled to 5° C., and the deposited crystals were collected by filtration. The crystals were added with acetone (200 mL), warmed to 50° C., and then filtered through a glass filter to remove the insoluble solids (step (B)). The filtrate was added with hexane (500 mL), and cooled to 5° C. The deposited crystals were collected by filtration, and then used in the step (C). In the step (C), the crystals were added with ethyl acetate (750 mL), dissolved at 65° C., stirred for 30 minutes, and then cooled to 5° C., and the deposited crystals were collected by filtration. The step (C) using ethyl acetate was similarly performed once more. The crystals were dissolved in ethyl acetate (750 mL), added with Kyoward 2000 (12 g) and Kyoward 700 (1 g) as adsorbents, and stirred at 60° C. for 1 hour. After the adsorbents were removed by filtration, the filtrate was cooled to 5° C., and the deposited crystals were collected by filtration (step (D)). In a similar manner, the treatment of the step (D) using adsorbents was performed twice. The crystals were washed with hexane (300 mL), then collected by filtration, and dried to obtain 38.2 g (yield: 54.6%) of the objective compound. As a result of TLC analysis performed in the same manner as in Synthesis Example 1, the purity was found to be 99.5%.

Example 1

Evaluation as Long Circulating Liposome in Blood (1) Preparation of Liposomes

Each of the lipids mentioned in each of the membrane compositions shown in Table 1 (Formulation Examples 1 to 6, Control Examples 1 and 2) were weighed in each ratio and dissolved in a chloroform/methanol mixture (2:1), then the organic solvents were evaporated by using an evaporator, and further the residue was dried under reduced pressure for 1 hour. Then, the dried lipids (lipid film) were added with 10 mL of 155 mM aqueous ammonium sulfate (pH 5.5) heated at 65° C. beforehand, and the mixture was lightly stirred by using a vortex mixer on a hot water bath (until lipid was substantially peeled off from a recovery flask). This lipid dispersion was transferred to a homogenizer, homogenized for 10 strokes and sized by using polycarbonate membrane filters with various pore sizes (0.2 μm×3 times, 0.1 μm×3 times, 0.05 μm×3 times and 0.03 μm×3 times) to prepare a dispersion of empty liposomes having a particle diameter of about 100 nm.

In an amount of 4 mL of this empty liposome dispersion was diluted 2.5 times with physiological saline, and the resulting diluted liposome dispersion was placed in an ultracentrifugation tube and centrifuged at 65,000 rpm for 1 hour. Then, the supernatant was discarded, and the precipitates were resuspended in physiological saline to make the dispersion volume 10 mL, the volume of the liposome dispersion before the centrifugation (at this time point, the total lipid concentration was adjusted to 50 mM). The aforementioned empty liposome dispersion in which the external aqueous phase was replaced with physiological saline (total lipid concentration: 50 mM) and a doxorubicin solution (medicament concentration: 3.3 mg/mL physiological saline) were heated beforehand at 60° C., and the empty liposome dispersion and the doxorubicin solution were added at a volume ratio of 4:6 (i.e., final medicament concentration: 2.0 mg/mL, final lipid concentration, 20 mM) and incubated at 60° C. for 1 hour. The mixture was further cooled at room temperature to obtain a doxorubicin-containing liposome dispersion.

(2) Physical Properties of the Liposome

The percentage of doxorubicin retained by the liposomes was obtained by collecting a part of the aforementioned liposome dispersion, subjecting the sample to gel filtration (Sephadex G-50, mobile phase was physiological saline), and then quantifying doxorubicin in the liposome fraction eluted in the void volume by using liquid chromatography. Further, particle diameter was determined by measurement based on the quasi-elastic light scattering QELS) method performed for a part of the aforementioned liposome dispersion. As a result, the percentage of doxorubicin, the active ingredient, encapsulated in liposomes was almost 100% in the case of Formulation Examples 4, 5 and 6 as shown in Table 1. Therefore, each original liposome dispersion was used without any treatment, and diluted 4/3 times with physiological saline for the experiment for evaluation of circulating in blood in rats described below (thus, final medicament concentration: 1.5 mg/mL, final lipid concentration: 15 mM). Further, the liposomes of Formulation Examples 1, 2 and 3 were subjected to ultracentrifugation (65,000 rpm, 1 hour) to remove unencapsulated medicament in the supernatant and then reconstituted with physiological saline so that a final medicament concentration of 1.5 mg/mL was obtained (thus, final lipid concentrations were about 16.9 mM in Formulation Example 1, about 17.1 mM in Formulation Example 2, and about 18.9 mM in Formulation Example 3). The particle diameters of the liposomes were around 100 nm for all the examples.

(3) Experiment for Evaluation of Circulating in Blood in Rats

An experiment for evaluation of circulating in blood was performed in SD male rats (6-week old) using Formulation Examples 1 to 6 and Control Examples 1 and 2 mentioned above. Each liposome dispersion was administered to rats from the cervical vein under ether anesthesia (each group consisted of 5 animals, dose: 7.5 mg doxorubicin/5 mL/kg), then blood was collected in heparin (0.5 to 1 mL) from the cervical vein under ether anesthesia at each blood collection time (2, 4, 8, 24, 48, 72, 120, 168 hours) and subjected to plasma skimming. Then, in a conventional manner, the blood was pretreated, and plasma medicament concentration was determined by HPLC. The AUC (0 to ∞) was calculated from the plasma medicament concentration obtained with each formulation of liposome dispersion according to the trapezoidal rule. As shown in Table 1, AUCs larger by 1 order or more were obtained with the liposome formulations containing the phospholipid derivatives of the present invention (Formulation Examples 1 to 6) compared with AUCs obtained with the liposomes of Control Example 1 not containing the lipid derivative of the present invention, and the liposomes of Control Example 2 added only with the phospholipid portion (DSPE: distearoylphosphatidylethanolamine) of the lipid derivative of the present invention, and thus clearly longer circulating in the blood was observed with the liposome formulations containing the phospholipid derivatives of the present invention.

TABLE 1

Physical properties and long circulating property in blood of liposomes

| | Liposome membrane composition | Particle size (nm) | Encapsulated efficiency of active ingredient (%) | $AUC_{0-\infty} \pm S.D$ (μg · hr/mL). |
|---|---|---|---|---|
| Formulation Example 1 | DSPE-MPE20H/HSPC/Cholesterol = 1.04 mM/ 11.28 mM/7.68 mM *DSPE-MPE20H: Synthesis Example 1 | 95 | 89.0 | 6980 ± 346 |
| Formulation Example 2 | DSPE-MEPE20H/HSPC/Cholesterol = 1.04 mM/ 11.28 mM/7.68 mM *DSPE-MEPE20H: Synthesis Example 5 | 92 | 87.7 | 5861 ± 612 |
| Formulation Example 3 | DSPE-MEP(R)20H/HSPC/Cholesterol = 1.04 mM/ 11.28 mM/7.68 mM *DSPE-MEP(R)20H: Synthesis Example 4 | 85 | 79.2 | 4158 ± 354 |
| Formulation Example 4 | DSPE-MPE20HCN/HSPC/Cholesterol = 1.04 mM/ 11.28 mM/7.68 mM *DSPE-MPE20HCN: Synthesis Example 3 | 84 | 100.0 | 5975 ± 302 |
| Formulation Example 5 | DSPE-MEPE20HCN/HSPC/Cholesterol = 1.04 mM/ 11.28 mM/7.68 mM | 83 | 100.0 | 6291 ± 473 |

TABLE 1-continued

Physical properties and long circulating property in blood of liposomes

| | Liposome membrane composition | Particle size (nm) | Encapsulated efficiency of active ingredient (%) | $AUC_{0-\infty} \pm S.D$ (μg · hr/mL). |
|---|---|---|---|---|
| Formulation Example 6 | *DSPE-MEPE20HCN: Synthesis Example 6 DSPE-MPE20HG/HSPC/Cholesterol = 0.56 mM/ 11.28 mM/7.68 mM | 69 | 100.0 | 8986 ± 501 |
| Control Example 1 | *DSPE-MPE20HG: Synthesis Example 2 HSPC/Cholesterol = 11.90 mM/ 8.10 mM | 91 | 100.0 | 452 ± 98 |
| Control Example 2 | DSPE/HSPC/Cholesterol = 1.04 mM/ 11.28 mM/7.68 mM | 94 | 100.0 | 397 ± 133 |

HSPC: Hydrogenated soybean phosphatidylcholine

Example 2

Preparation of Emulsion (Evaluation as Surfactant)

An emulsion was prepared by using the monomethyl-polyoxypropylene/polyoxyethylene-carbamyl (molecular weight: 2000)-distearoylphosphatidylethanolamine obtained in Synthesis Example 3. Specifically, among the base materials of the composition shown in Table 2, those of the oil phase containing an emulsifier were heated at 60° C. and uniformly dissolved, and then those of the aqueous phase were added at the same temperature with stirring to obtain an emulsion.

TABLE 2

| Oil phase: | |
|---|---|
| Cetanol | 2.0 wt % |
| Vaseline | 2.0 wt % |
| Squalane | 5.0 wt % |
| Stearic acid | 2 wt % |
| Hydrogenated soybean lecithin | 0.5 wt % |
| Liquid paraffin | 10.0 wt % |
| Polyoxyethylene (5 moles) monooleic acid ester | 1.5 wt % |
| Monomethyl-polyoxypropylene/polyoxyethylene-carbamyl (molecular weight: 2000)-distearoylphosphatidylethanolamine | 1.0 wt % |
| Tocopherol | 0.02 wt % |
| Perfume | As required |
| Preservative | As required |
| Aqueous phase: | |
| Propylene glycol | 5.0 wt % |
| Purified water | Balance |

The prepared emulsion successfully kept a stable emulsified state even after storage at 40° C. for 1 month.

INDUSTRIAL APPLICABILITY

The phospholipid derivative of the present invention can be used in an amount similar to the amount of ordinary polyethylene glycol-phospholipids, and the derivative can thicken the water shell of the surface of a liposome by suppressing the spreading of the polyalkylene oxide structure on the liposome surface and thereby increases the stability of the liposome. The phospholipid derivative of the present invention is also highly stable and highly safe for living bodies, and has a low coagulation point and thus has a favorable handling property at ordinary temperature. Therefore, the phospholipid derivative of the present invention can be suitably used in the fields of solubilization and dispersion of physiologically active substances and the like, drug delivery systems such as liposomes, and cosmetics.

What is claimed is:

1. A phospholipid derivative represented by the following formula (I):

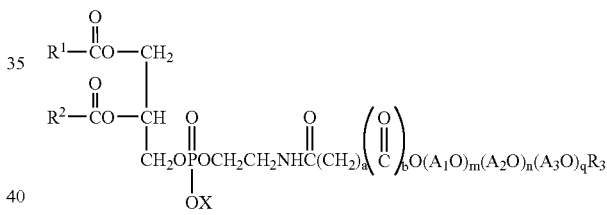

wherein $R^1CO$ and $R^2CO$ independently represent an acyl group having 8 to 22 carbon atoms; $R^3$ represents hydrogen atom, or a hydrocarbon group having 1 to 4 carbon atoms; symbol "a" represents an integer of 0 to 4; symbol "b" represents 0 or 1, provided that when a is 0, b is 0; X represents hydrogen atom, an alkali metal atom, an ammonium, or an organic ammonium; $A^1O$ and $A^3O$ independently represent an oxyalkylene group containing oxyethylene group and having 2 to 4 carbon atoms, wherein the ratio of the oxyethylene group to the oxyalkylene group having 2 to 4 carbon atoms in $A^1O$ and $A^3O$ is 0.5 or larger in terms of a weight ratio; $A^2O$ represents an oxyalkylene group having 3 or 4 carbon atoms; symbols "m" and "q" independently represent an average molar number of added oxyalkylene groups having 2 to 4 carbon atoms; and symbol "n" represent an average molar number of added oxyalkylene groups having 3 or 4 carbon atoms; provided that m, n and q satisfy the following conditions:

$5 \leq m \leq 600, 1 \leq n \leq 45, 0 \leq q \leq 200, 10 \leq m+n+q \leq 600,$
$0.04 \leq n/(m+n+q)$, and $q/(m+n+q) \leq 0.8.$ 2. A phospholipid derivative represented by the following formula (II):

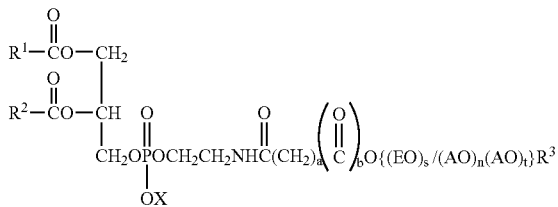

wherein R¹CO and R²CO independently represent an acyl group having 8 to 22 carbon atoms; $R^3$ represents hydrogen atom, or a hydrocarbon group having 1 to 4 carbon atoms; symbol "a" represents an integer of 0 to 4; symbol "b" represents 0 or 1, provided that when a is 0, b is 0; X represents hydrogen atom, an alkali metal atom, an ammonium, or an organic ammonium; EO represents oxyethylene group; AO represents an oxyalkylene group having 3 or 4 carbon atoms; {(EO)s/(AO)t} represents a group consisting of randomly bonded oxyethylene groups and oxyalkylene groups having 3 or 4 carbon atoms, wherein the ratio of the oxyethylene groups to the oxyalkylene groups having 2 to 4 carbon atoms in {(EO)s/(AO)t} is 0.5 to 0.95 in terms of a weight ratio; symbol "s" represents an average molar number of added oxyethylene groups; and symbol "t" represent an average molar number of added oxyalkylene groups having 3 or 4 carbon atoms; provided that s and t satisfy the following conditions:

$5 \leq s \leq 500$, $0 \leq t \leq 100$, and $6 \leq (s+t) \leq 500$.

3. The phospholipid derivative according to claim 1, wherein $A^1O$ and $A^3O$ are oxyethylene groups.

4. The phospholipid derivative according to claim 1, wherein $A^1O$ and $A^3O$ are oxyethylene groups, and $A^2O$ is oxypropylene group.

5. The phospholipid derivative according to claim 1, wherein $A^1O$ is oxyethylene group, $A^2O$ is oxypropylene group, and q is 0.

6. The phospholipid derivative according to claim 2, wherein AO is oxypropylene group, and the ratio of oxyethylene groups to oxyethylene groups and oxypropylene groups is 0.60 to 0.95.

7. A lipid membrane structure comprising the phospholipid derivative according to claim 1.

8. A pharmaceutical composition containing the lipid membrane structure according to claim 7 and a medicament.

9. The pharmaceutical composition according to claim 8, wherein the medicament is an antitumor agent.

10. A surfactant comprising the phospholipid derivative according to claim 1.

11. A lipid membrane structure comprising the phospholipid derivative according to claim 2.

12. A lipid membrane structure comprising the phospholipid derivative according to claim 3.

13. A lipid membrane structure comprising the phospholipid derivative according to claim 4.

14. A lipid membrane structure comprising the phospholipid derivative according to claim 5.

15. A lipid membrane structure comprising the phospholipid derivative according to claim 6.

16. A surfactant comprising the phospholipid derivative according to claim 2.

17. A surfactant comprising the phospholipid derivative according to claim 3.

18. A surfactant comprising the phospholipid derivative according to claim 4.

19. A surfactant comprising the phospholipid derivative according to claim 5.

20. A surfactant comprising the phospholipid derivative according to claim 6.

* * * * *

UNITED STATES PATENT AND TRADEMARK OFFICE
CERTIFICATE OF CORRECTION

PATENT NO. : 7,399,877 B2  Page 1 of 1
APPLICATION NO. : 10/549630
DATED : July 15, 2008
INVENTOR(S) : Itoh et al.

It is certified that error appears in the above-identified patent and that said Letters Patent is hereby corrected as shown below:

On the cover page of the printed patent, in (56) References Cited under Other Publications, in Alexander L. Klibanov et al., "Polyethyleneglycois" should read --Polyethyleneglycols--.

At column 23, line 8 (claim 2, line 10) of the printed patent, the formula: " "

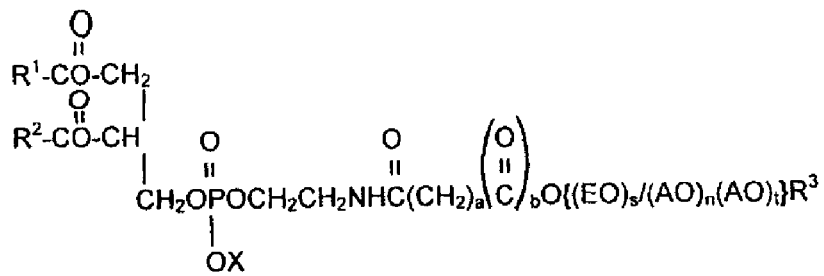

should be:

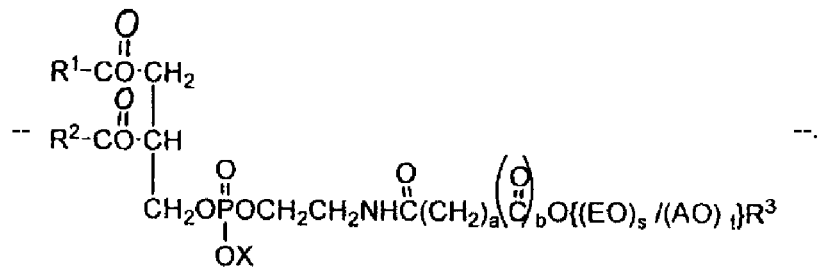

Signed and Sealed this

Twenty-eighth Day of April, 2009

JOHN DOLL
*Acting Director of the United States Patent and Trademark Office*